United States Patent
Boese et al.

(10) Patent No.: US 8,559,591 B2
(45) Date of Patent: Oct. 15, 2013

(54) METHOD AND DEVICE FOR RECORDING A PROJECTION DATASET OF AN OBJECT USING A PLURALITY OF X-RAY SOURCES

(75) Inventors: Jan Boese, Eckental (DE); Frank Dennerlein, Forchheim (DE)

(73) Assignee: Siemens Aktiengesellschaft, München (DE)

( * ) Notice: Subject to any disclaimer, the term of this patent is extended or adjusted under 35 U.S.C. 154(b) by 268 days.

(21) Appl. No.: 12/891,873

(22) Filed: Sep. 28, 2010

(65) Prior Publication Data

US 2011/0075809 A1 Mar. 31, 2011

(30) Foreign Application Priority Data

Sep. 29, 2009 (DE) .......................... 10 2009 043 420

(51) Int. Cl.
*G01N 23/00* (2006.01)
(52) U.S. Cl.
USPC .............................................. 378/9; 378/122
(58) Field of Classification Search
USPC ................................ 378/4–20, 122
See application file for complete search history.

(56) References Cited

U.S. PATENT DOCUMENTS

| | | | |
|---|---|---|---|
| 2005/0226371 A1* | 10/2005 | Kautzer et al. | 378/37 |
| 2007/0009081 A1* | 1/2007 | Zhou et al. | 378/10 |
| 2007/0025509 A1 | 2/2007 | Bani-Hashemi | |
| 2008/0056432 A1* | 3/2008 | Pack et al. | 378/4 |
| 2009/0022264 A1 | 1/2009 | Lalush | |

FOREIGN PATENT DOCUMENTS

DE 102008050353 5/2010

OTHER PUBLICATIONS

Maltz, et al., Fixed Gantry Tomosynthesis System for Radiation Theraphy Image Guidance Based on a Multiple Source X-Ray Tube With Carbon Nanotube Cathodes, Medical Physics, vol. 36, No. 5, May 2009, © 2009 Medical Association Physics Medical, pp. 1624-1636; Others.

* cited by examiner

*Primary Examiner* — Hoon Song

(57) ABSTRACT

A method for recording a projection dataset of a object to be recorded using a plurality of X-ray sources is provided, which X-ray sources are spaced apart from one another on average by an angle α relative to an isocenter. A plurality of projection images from different recording directions are recorded in succession while activating the corresponding X-ray sources. Two X-ray sources are activated in succession having a spacing of at least 2 α relative to the isocenter.

12 Claims, 2 Drawing Sheets

METHOD AND DEVICE FOR RECORDING A PROJECTION DATASET OF AN OBJECT USING A PLURALITY OF X-RAY SOURCES

CROSS REFERENCE TO RELATED APPLICATIONS

This application claims priority of German application No. 10 2009 043 420.8 filed Sep. 29, 2009, which is incorporated by reference herein in its entirety.

FIELD OF THE INVENTION

The invention relates to a method for recording a projection dataset of an object to be recorded and to a device for performing such a method.

BACKGROUND OF THE INVENTION

In 3D X-ray imaging, a sequence of two-dimensional projection images which have been acquired from different recording directions in relation to the object to be recorded is converted into a 3D representation of the object density by means of a tomosynthesis or CT algorithm. The achievable image quality of the 3D image is dependent to a significant degree on the type of data acquisition, in particular on the recording directions from which the projection images were recorded and on the associated recording times. In the prior art the different recording directions are generally arrived at by means of a mechanical movement of the recording system (medical C-arm, CT scanner). This means that the recording trajectory (the track through all recording positions) is traversed sequentially. Problems with this method are, for example, that movements during the recording create artifacts, and that a useful reconstruction is available only after the recording trajectory has been terminated completely.

The problem of cardiac movements is dealt with by means of ECG gating, for example, though this leads in some cases to extended recording times, since the movement of the X-ray source cannot be stopped during the unwanted cardiac phases. Moreover, mechanical movements can be replaced by innovative multi-pixel X-ray sources which in principle allow any desired switching of the X-ray focus.

SUMMARY OF THE INVENTION

It is the object of the present invention to provide a method for recording a projection dataset of an object to be recorded which permits a maximally artifact-free and rapid reconstruction of a projection image dataset into a 3D image; a further object of the invention is to provide an X-ray device that is suitable for performing the method.

The object is achieved according to the invention by means of a method and by a device as claimed in the independent claims. Advantageous embodiments of the invention are in each case the subject matter of the associated dependent claims.

The inventive method for recording a projection dataset of a object to be recorded using a plurality of X-ray sources, which X-ray sources are spaced apart from one another on average by an angle α relative to an isocenter, comprises the following steps: recording a plurality of projection images from different recording directions in succession while activating the corresponding X-ray sources, two X-ray sources activated in succession having a spacing of at least 2 α relative to the isocenter. No mechanical movements of the recording system are necessary in the case of the inventive method, so considerably fewer motion artifacts are produced than in the case of rotating systems. Furthermore, reconstructions can be performed already prior to a completed total recording of all the projection images of the projection dataset, with the result that a preliminary 3D image can already be available very quickly. This is possible owing to the fact that the projection recordings are not carried out one after another in ascending order in every possible recording direction, but rather that at most every second recording direction is used in direct succession so that a general overview over the entire range of recording directions is available much quicker.

According to an embodiment of the invention each two X-ray sources activated one after the other have a spacing of at least 2 α relative to the isocenter.

According to another embodiment of the invention the X-ray sources are activated stochastically or on a random basis. In this way there is a high probability that already after a small part of the projection images have been recorded sufficient projections from the most diverse recording directions will be present in order to produce a qualitatively good preliminary reconstruction of a 3D image.

Advantageously, each X-ray source is activated only once. This ensures that no superfluous repetitions can occur during the recording of projection images. Furthermore, each X-ray source is activated precisely once so that a high-quality 3D image can be reconstructed following completion of the recordings.

According to a further embodiment of the invention a controlled activation of the X-ray sources is performed in such a way that after an activation of a fraction 1/n of the X-ray sources, each two already activated X-ray sources essentially have a spacing of n α on average relative to the isocenter. By this means it is ensured that following the fraction 1/n of the total duration of the recording there are already sufficient projections from the entire range of the recording directions present in order to produce a qualitatively good reconstruction that is suitable for an overview. For example, following an activation of a quarter of the X-ray sources each two already activated X-ray sources can essentially have a spacing of 4 α on average relative to the isocenter. All in all, every fourth X-ray emitter is activated in this case in the first quarter of the recording, such that a rough reconstruction of a 3D image can be produced from said quarter of projection images. n can be an arbitrary whole number between 2 and 50.

A reconstruction of a 3D image from the projection dataset is beneficially performed following an activation of a fraction 1/n of the X-ray sources. Said 3D image is available already after a fraction of the recording and already provides a good general overview of the examination object. If further projection directions are available, the generated 3D image can be enhanced and improved at any time.

According to a further embodiment of the invention a first fraction of the X-ray sources is activated during a first phase, in particular cardiac phase, of a first cyclical movement, in particular of a first cardiac cycle, of a object to be recorded and a further fraction is activated during the same phase, in particular cardiac phase, of a further, in particular directly succeeding, cyclical movement, in particular of a cardiac cycle. In the case of a cardiac movement the projection images can in this way always be generated in relation to a specific, favorable cardiac phase so that no motion artifacts are produced and a preliminary reconstruction of a 3D image can be produced already after a first cardiac cycle. The remaining projection images can be produced in a corresponding cardiac phase of a second, third, fourth etc. cardiac cycle In addition to cyclical cardiac movements other cyclical movements, for example respiratory movements, can also be used in this way.

An X-ray system having a recording system comprising an X-ray detector and a plurality of X-ray sources which are spaced apart from one another on average by an angle α relative to the isocenter is suitable for performing the method according to the invention in conjunction with a control unit for targeted activation of the X-ray sources.

In this case each of the X-ray sources can be formed by a field emission gun having a field emission cathode. Field emission guns of said type can be produced in a particularly small and lightweight fowl. According to a further embodiment of the invention the field emission cathodes are formed on the basis of carbon nano tubes (referred to as CNT cathodes). Materials of said kind have a particularly good emission characteristic, are also stable at high currents, and furthermore can be manufactured in a particularly small format.

BRIEF DESCRIPTION OF THE DRAWINGS

The invention and further advantageous embodiments according to features of the dependent claims are explained in more detail below with reference to exemplary embodiments represented schematically in the drawing, without thereby restricting the invention to said exemplary embodiments; in the drawing:

DETAILED DESCRIPTION OF THE INVENTION

Figure 1:
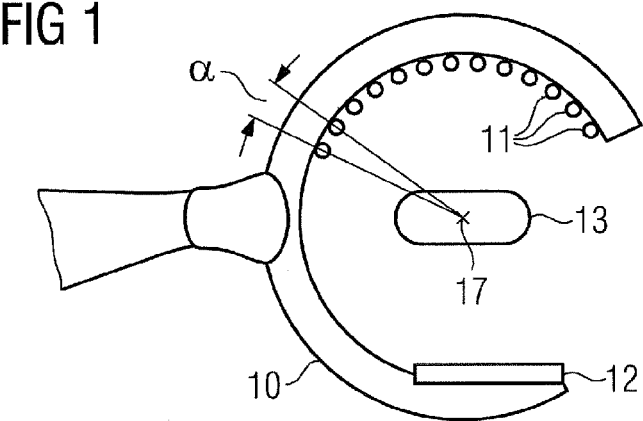
FIG. 1 shows a view of a detail from an X-ray system that is suitable for performing the method according to the invention.

FIG. 1 shows a detail from an X-ray system according to the invention having a C-arm 10 on which are mounted an X-ray detector and a plurality of X-ray emitters 11. In this case the X-ray emitters 11 are arranged in the circumferential direction along the C-arm 10 and are spaced apart from one another on average by an angle α relative to an isocenter, for example the center point 17 of the C-arm. The isocenter is a fixed reference point and can be defined, for example, as the point around which the C-arm would rotate if it were to be necessary to perform a mechanical movement for the purpose of recording the projection images from different recording directions. On average, in this context, means that the spacings do not have to match precisely for each X-ray source.

The X-ray emitters 11 are arranged for example in the form of a linear array on the C-arm and are all aligned in such a way that the X-ray beam generated by them is concentrated on the X-ray detector 12. When an examination object 13 is present, this is then traversed by the corresponding, currently activated X-ray beam and the thus filtered radiation is received by the X-ray detector and the resulting image data subsequently read out. A projection image is produced in this way.

Figure 5:
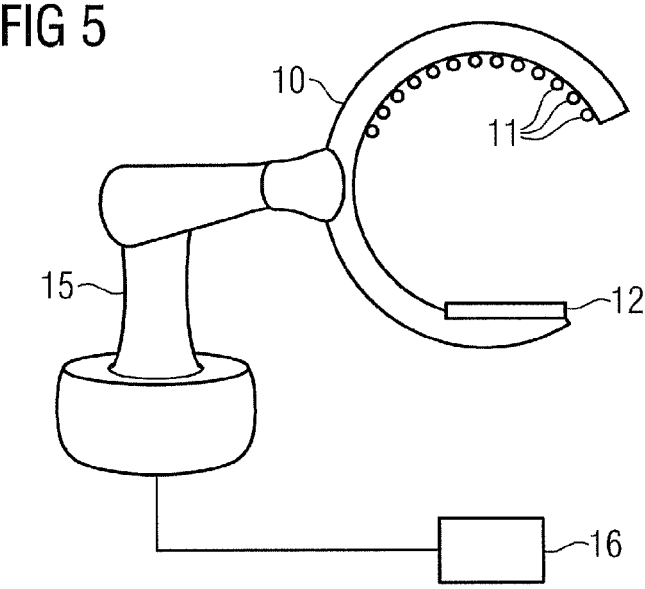
FIG. 5 shows a further view of a detail from an X-ray system that is suitable for performing the method according to the invention.

The X-ray emitters can advantageously be formed by field emission guns, each having a field emission cathode. Field emission guns of said type can be embodied so as to particularly small and effective, being implemented on the basis of carbon nano tubes, for example. FIG. 5 shows an X-ray system in which a C-arm as shown in FIG. 1 is arranged on what is termed an articulated-arm robot. This enables the C-arm to be moved in any rotatory and translational degrees of freedom. A control unit is provided for the purpose of controlling the X-ray emitters 11. Said control unit is embodied for activating the X-ray emitters in any sequence, that is to say for switching them in order to generate X-radiation. The X-ray detector is embodied for detecting the X-radiation each time an X-ray emitter is activated and for generating a projection image.

Figure 2:
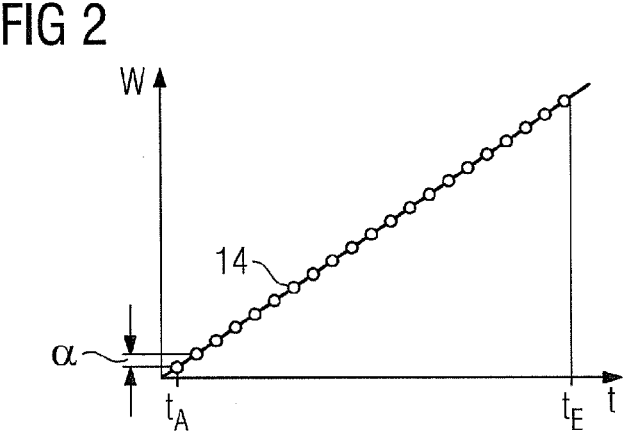
FIG. 2 shows a sequential recording sequence according to the prior art.

In known X-ray systems a single X-ray source is present; in order to record a dataset of projection images from different recording directions in such an X-ray system the X-ray source is rotated together with the X-ray detector around the examination object. In the X-ray system according to the invention it is possible to generate a dataset of projection images without mechanical movement by means of alternating X-ray emitters. One possible way of using an X-ray system comprising a plurality of X-ray emitters to obtain a comprehensive projection dataset which can be reconstructed into a 3D image consists in the following: starting with a first X-ray emitter, adjacent X-ray emitters are activated in turn in each case and in this way a projection image is obtained corresponding to a rotation sequentially from every possible recording direction. FIG. 2 shows a method of said kind having projection image recordings 14, the recording time t being plotted along the horizontal axis and the recording direction W in relation to a first, outer X-ray emitter being plotted along the vertical axis. Although this method has the advantage that hardly any motion artifacts are produced, it has the disadvantage that a useful reconstruction is possible only after the end of the recording of all the projection images, since only then is the entire range of recording directions, i.e. the entire trajectory, covered.

The method according to the invention provides a possible way of overcoming this disadvantage. With the method according to the invention, projection images are recorded from different recording directions, the average spacing of X-ray emitters activated in succession amounting to at least 2 α, i.e. after the first X-ray emitter, at the earliest the next-but-one adjacent X-ray emitter is reactivated etc. In this way it is possible to obtain projection images from recording directions distributed over the entire range of recording directions more quickly and consequently to enable a rough reconstruction to be produced already before the end of the acquisition of all of the projection images.

According to an embodiment of the invention the X-ray emitters are activated on a random basis during the recording of the dataset of projection images from the start of recording $t_A$ to the end of recording $t_E$. In this case, however, in particular each X-ray emitter is activated once, but no X-ray emitter is activated twice. The control unit, which is embodied for activating the X-ray emitters, activates a first randomly selected X-ray emitter so that a projection image can be recorded, then a second randomly selected X-ray emitter so that a second projection image will be recorded, then a third randomly selected X-ray emitter etc., until all the X-ray emitters have been activated once and a projection image has been recorded in relation to all of them.

Figure 3:
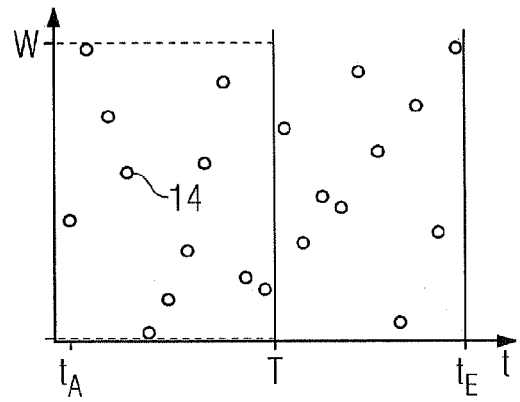
FIG. 3 shows a random recording sequence according to the invention.

Owing to the random selection the probability is very high that already after a part, such as e.g. a third, of the X-ray emitters, sufficient projections from the most diverse recording directions will be present in order to produce a reconstruction of a 3D image which allows the most important object structures of the examination object to be made visible. FIG. 3 shows a method having randomly activated X-ray emitters, wherein the projection image recordings 14 are drawn as points, the recording time t is shown along the horizontal axis and the recording direction W is shown along the vertical axis. At the time instant T, which in this case is arranged after half of the projection images, it is already possible to produce a high-quality preliminary reconstruction of a 3D image. As further projection images are added the preliminary 3D image converges toward the definitive reconstructed 3D image when the time instant T moves toward the end of recording $t_E$.

With said method, sequential images of a preliminary reconstruction can also be utilized for the purpose of detecting movement, e.g. for calculating a motion field, and the movement information can be applied to all the projection data at the end of recording $t_E$ (motion-compensated reconstruction).

According to another embodiment of the invention the X-ray emitters are controlled in such a way that following an activation of a fraction 1/n of the X-ray sources, each two already activated X-ray sources essentially have a spacing of n α on average. The control is chosen such that within a fraction of the time for the total recording time period, projection images can be acquired from markedly different directions. If said fraction is to amount to a quarter, for example, then on average every fourth X-ray emitter (e.g. in the case of a linear array) is activated and projection images are recorded: For example, the first X-ray emitter is activated and a projection image recorded, then the fifth X-ray emitter is activated and a projection image recorded, then the ninth X-ray emitter etc. At the end of the linear array a further pass is then performed either immediately or after a pause, starting with the second X-ray emitter for example. Pauses can also be inserted between the passes.

This embodiment of the invention is useful for example in the case of recurrent movements of the examination object in which projection data is to be recorded only within the short time period in which the dynamic object is in the desired state (prospective gating). An example of this is the movement of the heart when projection images are to be recorded only during a specific cardiac phase of the cardiac cycle. The first fraction of the projection images is recorded during the specific cardiac phase of the first cardiac cycle, then there is a pause; the second fraction is recorded during the same cardiac phase of the second cardiac cycle, a pause follows, then further fractions are recorded during further cardiac cycles. When the method according to the invention is used, a preliminary reconstruction can be performed already after the first fraction and hence the first cardiac cycle and as a result a preliminary 3D image is available.

Figure 4:
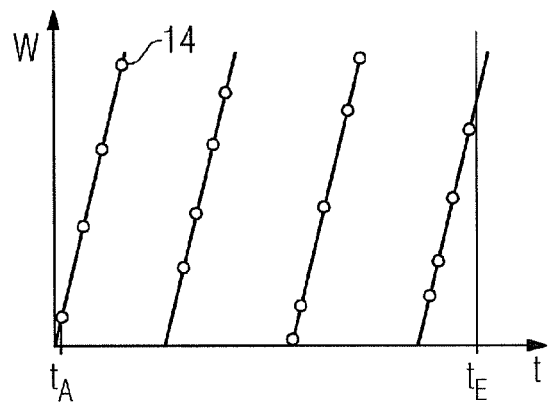
FIG. 4 shows a controlled recording sequence according to the invention.

FIG. 4 shows a controlled method according to the described embodiment, wherein in this case instead of every fourth X-ray emitter being activated, projection images distributed equally over the entire range of the recording directions are recorded during each fraction.

Figure 6:
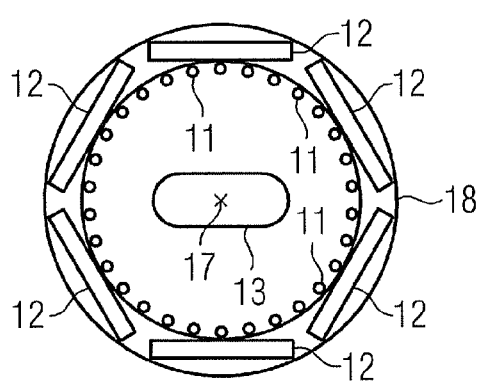
FIG. 6 shows a view of a computed tomography system having a plurality of X-ray emitters.

The method according to the invention can be used for example for standard 3D recording or computed tomography or also for tomosynthesis. For example, a tomosynthesis X-ray device can have, as shown in FIG. 1, a C-arm and X-ray sources arranged thereon. FIG. 6 shows a computed tomography X-ray device which has a gantry 18 in which are arranged a plurality of X-ray sources 11 which are distributed over the entire angular range of 360°. The gantry 18 also has a plurality of X-ray detectors likewise extending over the entire angular range. Alternatively, an X-ray detector 12 that is rotatable inside the gantry can also be provided.

The invention includes the use of an X-ray system comprising a plurality of X-ray sources in order to enable an arbitrary, non-mechanical and non-sequential switching of the viewing positions during the recording of the projection dataset with the aim of obtaining new imaging features or improving image quality. The method permits progressive 3D Imaging and improved prospective gating for the purpose of reconstructing dynamic objects.

The invention can be briefly summarized as follows: The invention provides a method for recording a projection dataset of a object to be recorded using a plurality of X-ray sources, which X-ray sources are spaced apart from one another on average by an angle α relative to an isocenter, the method comprising the following steps: recording a plurality of projection images from different recording directions in succession while activating the corresponding X-ray sources, two X-ray sources activated in succession having a spacing of at least 2 a relative to the isocenter.

The invention claimed is:

1. A method for recording a projection dataset of an object using a plurality of X-ray sources spaced apart from one another on average by an angle α relative to an isocenter, comprising:
    activating at least two of the X-ray sources in a succession having a spacing of at least 2 α relative to the isocenter; and
    recording a fraction of the projection dataset in the succession from different recording directions while activating the at least two of the X-ray sources,
    wherein a preliminary 3D image is reconstructed from the fraction of the projection dataset after 1/n of the X-ray sources are activated before end of the recording of all the projection dataset, and
    wherein the preliminary 3D image is enhanced and improved after further projection directions are available.

2. The method as claimed in claim 1, wherein each two of the X-ray sources activated one after the other have a spacing of at least 2 α relative to the isocenter.

3. The method as claimed in claim 1, wherein the X-ray sources are activated stochastically or randomly.

4. The method as claimed in claim 1, wherein each of the X-ray sources is activated only once.

5. The method as claimed in claim 1, wherein each two of the X-ray sources activated one after the other have a spacing of n α relative to the isocenter after 1/n fraction of the X-ray sources are activated.

6. The method as claimed in claim 1, wherein each two of the X-ray sources activated one after the other have a spacing of 4 α relative to the isocenter after a quarter of the X-ray sources are activated.

7. The method as claimed in claim 1, wherein a first fraction of the X-ray sources is activated during a phase of a first cyclical movement of the object and a further fraction of the X-ray sources is activated during the same phase of a further cyclical movement.

8. The method as claimed in claim 7, wherein the cyclical movement comprises a respiratory movement.

9. The method as claimed in claim 1, wherein a first fraction of the X-ray sources is activated during a first cardiac phase of a first cardiac cycle of the object and a further fraction of the X-ray sources is activated during the same cardiac phase of a further cardiac cycle.

10. An X-ray system for recording a projection dataset of an object, comprising:
    a plurality of X-ray sources spaced apart from one another on average by an angle α relative to an isocenter;

a control unit that activates at least two of the X-ray sources in a succession having a spacing of at least 2 α relative to the isocenter; and an X-ray detector that records a fraction of the projection dataset in the succession from different recording directions while activating the at least two of the X-ray sources, wherein a preliminary 3D image is reconstructed from the fraction of the projection dataset after 1/n of the X-ray sources is activated before end of the recording of all the projection dataset, and wherein the preliminary 3D image is enhanced and improved after further projection directions are available.

11. The X-ray system as claimed in claim 10, wherein the X-ray sources comprises field emission guns having field emission cathodes.

12. The X-ray system as claimed in claim 11, wherein the field emission cathodes comprise a nanostructured material comprising carbon nano tubes.

* * * * *